United States Patent [19]

Staller

[11] Patent Number: 4,540,721

[45] Date of Patent: Sep. 10, 1985

[54] METHOD OF PROVIDING ODOR TO PRODUCT CONTAINER

[75] Inventor: Kerry P. Staller, Loveland, Ohio

[73] Assignee: The Procter & Gamble Company, Cincinnati, Ohio

[21] Appl. No.: 474,102

[22] Filed: Mar. 10, 1983

[51] Int. Cl.³ .............. B65D 5/08; C08K 5/00; C11B 9/00; A61K 7/46

[52] U.S. Cl. .............. 523/102; 53/396; 252/522 A; 239/54; 239/55; 493/148; 524/354; 524/356

[58] Field of Search .............. 523/102; 252/522 A; 239/55, 54; 53/396; 493/148; 524/354, 356

[56] References Cited

U.S. PATENT DOCUMENTS

| | | | |
|---|---|---|---|
| 2,397,817 | 4/1946 | Staunton et al. | 167/37 |
| 2,963,454 | 12/1960 | Drugge et al. | 524/21 |
| 3,505,432 | 4/1970 | Neuwald | 523/102 |
| 3,553,296 | 1/1971 | Gaeckel | 523/102 |
| 3,565,831 | 2/1971 | Lubbecke | 252/522 |
| 3,567,118 | 3/1971 | Shepherd et al. | 239/54 |
| 3,567,119 | 3/1971 | Wilbert et al. | 239/6 |
| 3,596,833 | 8/1971 | Gould | 239/54 |
| 3,655,129 | 4/1972 | Seiner | 239/60 |
| 3,685,734 | 8/1972 | Paciorek et al. | 239/56 |
| 3,688,985 | 9/1972 | Engel | 239/54 |
| 3,711,024 | 1/1973 | Hammond | 239/55 |
| 3,772,215 | 11/1973 | Gould et al. | 252/522 |
| 3,775,227 | 11/1973 | Wilbert et al. | 161/30 |
| 3,804,796 | 4/1974 | Alexandre | 523/102 |
| 3,919,138 | 11/1975 | Keegan et al. | 523/102 |
| 3,939,099 | 2/1976 | Tusa et al. | 252/522 |
| 3,971,852 | 7/1976 | Brenner et al. | 252/522 A |
| 4,051,159 | 9/1977 | Tsoucalas et al. | 523/102 |
| 4,095,031 | 6/1978 | Eagle | 526/1 |
| 4,110,261 | 8/1978 | Newland | 252/322 |
| 4,160,750 | 7/1979 | Columbus et al. | 523/102 |
| 4,170,585 | 10/1979 | Motegl et al. | 524/762 |
| 4,184,099 | 1/1980 | Lindauer et al. | 313/315 |
| 4,209,417 | 6/1980 | Whyte | 252/174.11 |
| 4,257,176 | 3/1981 | Hartung et al. | 36/44 |
| 4,339,356 | 7/1982 | Whyte | 252/522 A |
| 4,362,841 | 12/1982 | Minatono et al. | 252/522 A |

FOREIGN PATENT DOCUMENTS

| | | | |
|---|---|---|---|
| 0004463 | 10/1979 | European Pat. Off. | |
| 0084821 | 8/1983 | European Pat. Off. | |
| 825293 | 12/1951 | Fed. Rep. of Germany | |
| 115693 | 10/1975 | German Democratic Rep. | |
| 46911 | 11/1972 | Japan | |
| 49-99731 | 9/1974 | Japan | 523/102 |
| 20055 | 2/1981 | Japan | |
| 12610 | of 1886 | United Kingdom | |
| 1206047 | 9/1970 | United Kingdom | |
| 2085463 | 4/1982 | United Kingdom | |
| 2093856 | 9/1982 | United Kingdom | 523/102 |

OTHER PUBLICATIONS

Chemical Abstracts 89: 130476h Perfumes for Cyanoacrylate Adhesives.
Chemical Abstracts 90: 105142j α-Cyanoacrylate Adhesives Containing Perfumes.

*Primary Examiner*—Ronald W. Griffin
*Attorney, Agent, or Firm*—Leonard Williamson; Milton B. Graff, IV; Richard C. Witte

[57] ABSTRACT

A method is presented for using scented oils to provide odor to a container of a product having a constituent incompatible with the scented oils. An aqueous emulsion which comprises from about 4% to about 70% of a water-emulsifiable or water-soluble polymer, from about 5% to about 80% of scented oils, and from about 6% to about 80% of water is prepared. The aqueous emulsion is dried whereby the scented oils are entrapped within the matrix of the polymer. The polymer matrix is included in the container with the product whereby the scented oils are protected by the polymer matrix from degradation by the incompatible constituent and diffuse from the polymer matrix over a period of time.

40 Claims, No Drawings

METHOD OF PROVIDING ODOR TO PRODUCT CONTAINER

TECHNICAL FIELD

This invention relates to altering the odor emanating from a product container by entrapping scented oils in a polymer matrix within the container.

BACKGROUND OF THE INVENTION

The use of scented or essential oils as perfumes in a wide variety of products to impart a desired odor to the products is very common. However, the use of certain scented oils in some products is precluded due to incompatability between the scented oils and the products. In particular, many scented oils are susceptible to degradation due to oxidation. Therefore, it can be difficult to impart desired odor characteristics to products having oxidizing properties due to the presence of oxidative constituents. One class of products that is particularly difficult to impart desired odor characteristics to because of their oxidative constituents are products containing dry bleaches.

Consumer objection to unpleasant product odors can often be substantially reduced by providing a pleasant odor in the headspace of the product container to mask an unpleasant product odor. One potential method for imparting desired odor characteristics to the headspace of the container of such products is to impart the desired odor to the container rather than to the product. Such a method is disclosed in European Patent Application Publication No. 0,004,463 A2 published on Oct. 3, 1979, where perfume is sprayed on an absorbent material, such as the product carton itself, from which it diffuses into the headspace of the carton. A similar method is disclosed in U.S. Pat. No. 3,711,024 issued to Hammond on Jan. 16, 1973, for imparting a desired odor to the product contained in the carton (in this case tissues).

The present invention involves forming an adhesive aqueous emulsion of scented oils, polymer, and water which upon drying entraps a high level of scented oils in a polymer matrix. The polymer matrix with entrapped scented oils can be included in a product container where the scented oils slowly diffuse from the polymer matrix over an extended period of time to provide the desired odor characteristics in the product container, particularly in the headspace. The scented oils entrapped within the polymer matrix are protected from the product so that oxidative degradation of the scented oils does not occur.

Perfumes have been incorporated in adhesive polymeric substances; the most common purpose is to mask the odor of the adhesive. Examples of references which disclose such perfumed adhesives include U.S. Pat. Nos. 2,397,817 issued to Staunton, Close and Hess on Apr. 2, 1946; 2,963,454 issued to Drugge and Hine on Dec. 6, 1960; 3,919,138 issued to Keegan, Patel and Rubin on Nov. 11, 1975; 4,160,750 issued to Columbus and Anderson on July 10, 1979; and 4,170,585 issued to Motegi and Kimura on Oct. 9, 1979; British Patent application No. 2,085,463 issued on Apr. 28, 1982; and Japanese Pat. Nos. 99,731 issued on Sept. 20, 1974, 46,911 issued on Nov. 27, 1972, 58,591 issued on May 26, 1978, and 123,442 issued on Oct. 27, 1978.

Molded polymeric objects having relatively high levels of perfume entrapped within the polymers are disclosed in the following references: U.S. Pat. Nos. 3,505,432 issued to Neuwald on Apr. 7, 1970; 3,553,296 issued to Gaeckel on Jan. 5, 1971; 4,051,159 issued to Tsoucalas, Barclay and Rogers on Sept. 27, 1977; 4,095,031 issued to Engle on June 13, 1978; 4,110,261 issued to Newland on Aug. 29, 1978; 4,184,099 issued to Lindauer, Munteanu, Reich, and Pelliza on Jan. 15, 1980; and 4,257,176 issued to Hartung and Siegel on Mar. 24, 1981; and Japanese Pat. No. 20,055 issued on Feb. 25, 1981.

Thin layers or films of polymeric materials containing scented oils are disclosed in U.S. Pat. Nos. 3,655,129 issued to Seiner on Apr. 11, 1972; 3,685,734 issued to Paciorek and Norton on Aug. 22, 1972; and 3,939,099 issued to Tusa and Tranner on Feb. 17, 1976. Seiner discloses the making of a scented polymeric film by dispersing small particles of polymer with cells of scented oils within the polymer in an aqueous emulsion and then spreading the emulsion on a surface to dry thereby forming such film. Tusa and Tranner discloses an alcohol-water solution containing polymer and perfume which is applied to human skin to achieve odor release over an extended time period.

U.S. Pat. No. 3,565,831 issued to Detert on Feb. 23, 1971, discloses a Christmas tree spray containing perfume, alcohol solvent, cellulose ether, and rosin which is used to impart a pine odor to artificial Christmas trees.

U.S. Pat. No. 3,688,985 issued to Engle on Sept. 5, 1972, discloses the impregnation of fragrance in molded plastic objects by contact with an aqueous emulsion containing about 10% scented oil. The emulsion may contain polyvinyl alcohol as a protective colloid. British Pat. No. 12,610 issued on Oct. 4, 1886, discloses solid perfume products made by the addition of at least 25% scented oils to a water-based paste of certain mineral salts.

U.S. Pat. No. 3,775,227 issued to Wilber and Brown on Nov. 27, 1973, discloses formulations in which up to 45% essential oils are mixed with aqueous-based polymer emulsions containing finely divided absorbent particles. Such mixtures are used to coat molded plastic objects in order to provide them with a long lasting odor. The emulsions are prepared at relatively low temperatures to prevent thermal degradation of the fragrant oils.

SUMMARY OF THE INVENTION

It is an object of the present invention to provide a method for attaining desired odor characteristics emanating from product containers.

It is a further object of the present invention to provide such odor characteristics by entrapping scented oils in a polymer matrix which can be incorporated in such product containers.

It is still a further object of the present invention to provide such scented oils entrapped in a polymer matrix such that the scented oils are protected from degradation in the container by a constituent of the product which is incompatible with the scented oils.

It is also an object of the present invention to provide a high level of scented oils entrapped in a polymer matrix in order to provide a sufficient odor released over an extended period of time in such product containers.

These and other objects will become apparent from the detailed description of the invention.

The invention described herein is a method for using scented oils to provide odor to a container of a product having a constituent incompatible with the scented oils. An aqueous emulsion is prepared which comprises from about 4% to about 70% of a water-emulsifiable or water-soluble polymer, from about 5% to about 80% of scented oils, and from about 6% to about 80% of water. The aqueous emulsion is dried, whereby the scented oils are entrapped within a matrix of the polymer. The polymer matrix is included in the container with the product, whereby the scented oils are protected by the polymer matrix from degradation by the incompatible constituent and diffuse from the polymer matrix over a period of time.

DETAILED DESCRIPTION OF THE INVENTION

The present invention involves a method for imparting a desired odor in containers of product. The product may be a material or mixture of materials. Use of the present invention is contemplated primarily when the scented oils which provide the desired odor are incompatible with a constituent of the product in the container. This often occurs when the product contains chemically reactive constituents, especially oxidative constituents, since many scented oils are readily oxidized and thereby degraded by such substances.

Oxidative Dry Bleach Constituents

Applicant has particularly found the present invention useful for incorporating a desired odor in the headspace of containers containing products having dry bleach constituents which are oxidative compounds. Examples of such dry bleach constituents include organic preoxygen bleaches, hypochlorite bleaches, sodium perborate, sodium perborate tetrahydrate, sodium percarbonate, potassium monopersulfate, urea peroxide, potassium dichlorocyanurate, sodium dichlorocyanurate dihydrate, and the like.

Hypochlorite bleaches include any compound which provides the hypochlorite ion ($OCl^-$) in aqueous solution. Such compounds include alkaline metal and alkaline earth metal hypochlorites, hypochlorites addition products, chloramines, chlorimines, chloramides, and chlorimides. Specific examples of compounds of this type include sodium hypochlorite, potassium hypochlorite, lithium hypochlorite, calcium hypochlorite, calcium hypochlorite dihydrate, monobasic calcium hypochlorite, dibasic magnesium hypochlorite, chlorinated trisodium phosphate dodecahydrate, potassium dichloroisocyanurate, sodium dichloroisocyanurate, sodium dichloroisocyanurate dihydrate, 1,3-dichloro-5,5-dimethylhydantoin, N-chlorosufamide, Chloramine T, Dichloramine T, Chloramine B, and Dichloramine B. Mixtures of such compounds may be used as dry bleach constituents.

Organic peroxygen bleaches include such compounds as peroxyacid compounds and the like. The present invention is particularly suitable for use with products containing peroxyacid compounds. Such peroxyacid compounds are the organic peroxyacids and water-soluble salts thereof which in aqueous solution yield a species containing a $-O-O^-$ moiety. These materials have the general formula

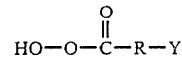

wherein R is an alkylene group containing from 1 to about 20 carbon atoms or a phenylene group, and Y is hydrogen, halogen, alkyl, aryl, or any group which provides an anionic moiety in aqueous solution. Such Y groups can include, for example,

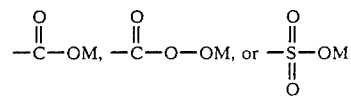

wherein M is H or a water-soluble, salt-forming cation.

The organic peroxyacids and salts thereof can contain one or more peroxy groups and can be either aliphatic or aromatic. When the organic peroxyacid is aliphatic, the unsubstituted acid has the general formula

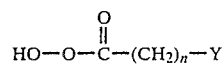

where Y, for example, can be $-CH_3$, $-CH_2Cl$,

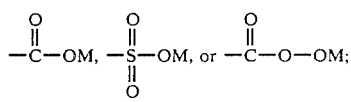

and n can be an integer from 1 to 20. The alkylene linkage and/or Y (if alkyl) can contain halogen or other noninterfering substituents.

When the organic peroxyacid is aromatic, the unsubstituted acid has the general formula

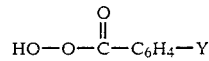

wherein Y is hydrogen, halogen, alkyl,

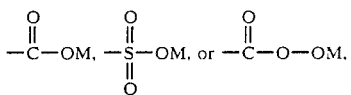

for example. The percarboxy and Y groupings can be in any relative position around the aromatic ring. The ring and/or Y group (if alkyl) can contain any noninterfering substituents such as halogen groups. Examples of suitable aromatic peroxyacids and salts thereof include monoperoxyphthalic acid, diperoxyterephthalic acid, 4-chloroperoxyphthalic acid, the monosodium salt of diperoxyterephthalic acid, m-chloroperoxybenzoic acid, p-nitroperoxybenzoic acid, and diperoxyisophthalic acid.

The present invention is most useful with products containing dry bleach constituents containing aliphatic diperoxyacids, especially those having from about 6 to about 20 carbon atoms. Such aliphatic diperoxyacids have the general formula

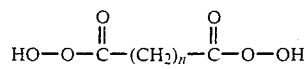

wherein n is from about 4 to about 18.

Method for Including Scented Oils in a Product Container

Products containing reactive constituents may have odors which are considered unpleasant by consumers. Scented oils (also often termed essential oils, fragrance oils, or perfumes) are frequently used to provide a desired odor for many products. However, such scented oils may be readily degraded by such reactive constituents, especially oxidative compounds. When added directly to a product containing a reactive constituent, such scented oils are often rapidly degraded such that they no longer impart the desired odor to the product.

For many products which incorporate oxidative constituents such as dry bleaches, laundry products for example, the odor of the product is noticed primarily when handling it in its immediate storage and usage container. For laundry products, the container is often a cardboard carton. The odor of the product is especially noticeable when the carton is first opened. The odor will also likely be noticed when the consumer takes the carton and pours product from it. Because such products are often so closely associated with their immediate container, an effective means of masking an unpleasant odor of the product is to provide a masking odor in the headspace of the product container.

The present invention involves the inclusion of scented oils in a product container and the protection of the scented oils from degradation while in the container. An aqueous emulsion comprising a polymer, scented oils, and water may be prepared by the following preferred procedure. A viscous fluid or paste is made by mixing together a water-emulsifiable or water-soluble polymer and water. The scented oils are then mixed with the polymer/water mixture thus producing the aqueous emulsion. Although not necessarily limiting the present invention to such a mechanism, it has been found that particularly suitable polymer/scented oil/water emulsions are obtained when the polymer and scented oils are miscible. When the water is removed from the aqueous emulsion by drying, the scented oils are entrapped within a matrix of the polymer. The polymer matrix with scented oils entrapped can be included in a container of the product to provide a pleasant odor and to mask the product odor, if needed. The polymer matrix protects the scented oils from reactive constituents of the product. The scented oils diffuse from the polymer matrix over a period of time, generally several months, to provide the desired odor emanating from the product container.

It is highly desirable that the polymer/scented oil/water emulsion have adhesive properties. The emulsion can then be applied to the surface of a material and dried such that the resulting polymer matrix with entrapped scented oils is adhered to the material. The material can be included in the product container. The material surface to which the emulsion is applied can be any convenient material that the dried polymer matrix will adhere to, such as cardboard, paper, plastic, etc. The material surface to which the emulsion is applied is preferably an interior surface of the product container itself. Where, as is commonly the case, the product container is a cardboard carton, the emulsion is preferably applied to the carton surface that will be the interior of the top of a carton, when the carton is filled with product and sealed shut. This positions the polymer matrix with entrapped scented oils to provide the maximum odor to the headspace of the completed carton containing product. Although the interior of the top of the carton provides the optimum placement for the polymer matrix containing entrapped scented oils, the matrix may be located on any interior surface of the container, or on the surface of a separate piece of material which is included in the container. If the polymer/scented oil/water emulsion has sufficient adhesive properties, it may be used as an adhesive for adhering parts of the container together. Other means of including the polymer matrix in a product container may be employed.

The scented oils used to provide odors in the present invention are frequently susceptible to degradation or substantial loss of volatile components at high temperatures. Therefore, it is preferred that the polymer/scented oil/water emulsion be prepared and dried at a temperature sufficiently low to avoid substantial degradation or loss of the scented oils, preferably below about 35° C.

The polymer matrix with entrapped scented oils of the present invention is generally a rubbery solid at the ambient temperatures at which products are normally stored. It is preferred that the dried polymer matrix be non-tacky within the range of temperatures at which the product is to be stored so that the product in the container does not stick to exposed polymer matrix.

Water-Emulsifiable or Water-Soluble Polymer

The polymers that can be usefully employed in the present invention are those that are emulsifiable or soluble in water, preferably emulsifiable in water, at or near ambient temperatures. Particular polymers which can be utilized in the present invention include vinyl polymers including carbonyl or alcohol chemical groups; examples of such polymers include polyvinyl acetate, polyacrylate, polymethacrylate, and polyvinyl alcohol. Preferred polymers for use in the present invention include polyvinyl acetate, polyacrylate, and polymethacrylate; especially preferred is polyvinyl acetate. Various rubber polymers may also be useful with respect to the present invention. Examples of such rubber polymers include natural rubber, styrene-butadiene rubber, butyl rubber, neoprene rubber, and nitrile rubber. Mixtures of compatible polymers can be readily used as well as a single polymer.

The quantity of water-emulsifiable or water-soluble polymer that can be incorporated in the aqueous emulsions of the present invention varies from about 4% to about 70% of such emulsions. The preferred content of such polymers in the emulsions is from about 4% to about 40%; more preferred is from about 10% to about 35%; especially preferred is from about 20% to about 30%.

Scented Oils

The scented oils which may be incorporated in the aqueous emulsions of the present invention include a wide variety of odoriforous materials also known as essential oils, fragrance oils, or perfumes. When the scented oils are mixed with the polymer/water mixture as indicated hereinabove, a stable, preferably adhesive emulsion results.

A large variety of scented oils may be used in formulations of the present invention depending on the masking odor desired. The scented oils would be selected according to the desires of the formulator. The scented oils employed herein will most often be liquid at ambient temperatures, but also can be solids such as the various camphoraceous perfumes known in the art. A wide variety of chemicals are known for perfumery uses, including materials such as aldehydes, ketones, esters, and the like. More commonly, naturally-occurring plant and animal oils and exudates comprising complex mixtures of various chemical components are known for use as perfumes, and such materials can be used as scented oils herein. The scented oils herein can be relatively simple in their composition, or can comprise highly sophisticated, complex mixtures of natural and synthetic chemical components, all chosen to provide any desired odor.

Typical scented oils herein can comprise, for example, woody/earthy bases containing exotic materials such as sandalwood oil, civet, patchouli oil, and the like. The scented oils herein can be of a light, floral fragrance, e.g., rose extract, violet extract, and the like. Scented oils herein can be formulated to provide desirable fruity odors, e.g. lime, lemon, orange, and the like.

The quantity of scented oils present in the aqueous emulsions of the present invention varies from about 5% to about 80% of such emulsions. The preferred quantity of scented oils present in such emulsions varies from about 45% to about 80%; more preferred is from about 45% to about 65%; especially preferred is from about 45% to about 55%.

Water

The aqueous emulsions of the present invention are preferably produced by first preparing a mixture of a polymer as specified hereinabove in water. Such mixture preferably contains from about 30% to about 80% water. The scented oils are then added to the polymer/water mixture with mixing to provide the aqueous emulsions of the present invention. Such emulsions contain from about 6% to about 80% water. The preferred quantity of water in emulsions of the present invention is from about 6% to about 45%; more preferred is from about 15% to about 40%; especially preferred is from about 20% to about 30%.

Method of Manufacture

A method of making formulations of the present invention is described in Example 1 which follows.

Industrial Applicability

The present invention is advantageously used to mask unpleasant product odors emanating from containers of a product. For example, a polymer matrix with entrapped scented oils can be coated on the inside of the top of a carton of a product to provide a pleasant odor in the headspace of the carton.

The following examples will illustrate the invention, but are not intended to be any way limiting thereof.

EXAMPLE 1

General purpose white resin glue containing 52% polyvinyl acetate solids in water, Resyn 31-7014 supplied by National Starch and Chemical Corporation of Bridgewater, N.J., is used as the polymer/water mixture. Five hundred grams of the glue is added to the bowl of a planetary mixer such as a Kitchenaid Model K4555 supplied by Hobart Corporation of Troy, Ohio. Five hundred grams of Perfume A is blended into the glue in incremental 100 gram portions with thorough mixing after each portion is added. Perfume A is a blend of scented oils having an odor described by a perfumer as "powdery floral". The resulting glue/perfume mixture is a thick, stable, adhesive emulsion. Two grams of the emulsion is applied to the interior surface of the first-down major flap of a cardboard carton and is allowed to dry at ambient room temperature to a clear, rubbery, non-tacky solid which is strongly adhered to the cardboard. The carton is filled with a laundry product containing a dry bleach constituent, diperoxydodecanoic acid. The top of the carton is sealed with adhesive. Perfume A diffuses from the rubbery solid to provide a pleasant odor to the headspace of the carton for several months.

EXAMPLE 2

Ten grams of the white resin glue of Example 1 is added to a small jar. Ten grams of Perfume B is added to the glue in two gram increments. The glue/perfume mixture is thoroughly hand stirred with a spatula after the addition of each increment of perfume. Perfume B, a perfume with components of high volatility, is a blend of scented oils having an odor described by a perfumer as "aldehydric citrus". The resulting glue/perfume mixture is a thick, stable, adhesive emulsion. The emulsion is applied to cardboard and allowed to dry at ambient room temperature. The dried polymer matrix containing Perfume B is a rubbery solid with a non-tacky surface which is strongly adhered to the cardboard. Perfume B diffuses from the rubbery solid providing it with odor for several months.

EXAMPLE 3

Ten grams of the white resin glue of Example 1 is added to a small jar. Ten grams of Perfume C is added to the glue in two gram increments. The glue/perfume mixture is thoroughly hand stirred with a spatula after the addition of each increment of perfume. Perfume C, a perfume with components of low volatility, is a blend of scented oils having an odor described by a perfumer as "woody spice floral". The resulting glue/perfume mixture is a thick, stable, adhesive emulsion. The emulsion is applied to cardboard and allowed to dry at ambient room temperature. The dried polymer matrix containing Perfume C is a rubbery solid with a non-tacky surface which is strongly adhered to the cardboard. Perfume C diffuses from the rubbery solid providing it with odor for several months.

EXAMPLE 4

Eighty grams of Perfume A is added to a high speed blender, Model 31BL92 supplied by Waring Products Division, Dynamics Corporation of America of New Hartford, Conn. Twenty grams of the white resin glue of Example 1 is added to the blender and the blender is turned on. The blender blades slow as it mixes indicating a viscosity increase of the glue/perfume mixture. The resulting glue/perfume mixture is thick, stable, adhesive emulsion. When the emulsion is applied to cardboard and allowed to dry at ambient room temperature, the resulting rubbery solid containing Perfume A has a tacky surface. When incorporated in a carton of the product of Example 1, portions of the product stick to the polymer matrix. Perfume A diffuses from the rubbery solid providing it with odor for several months.

EXAMPLE 5

Ten grams of a 50% solids polyacrylate/water mixture, product code E1179N supplied by Rohm and Haas Company, Philadelphia, Pa., is added to a small jar. Ten grams of Perfume A is added to the mixture without stepwise addition and is hand stirred with a spatula to form a homogeneous emulsion. The emulsion exhibits partial separation after a few hours standing at ambient temperature. The fresh mixture adheres well to cardboard and dries at ambient room temperature to form a non-tacky solid which is strongly adhered to the cardboard. Perfume A diffuses from the solid providing it with odor for several months.

While particular embodiments of the present invention have been illustrated and described, it would be obvious to those skilled in the art that various changes and modifications can be made without departing from the spirit and scope of the invention. It is intended to cover, in the appended claims, all such modifications that are within the scope of this invention.

What is claimed is:

1. A method for using scented oils to provide odor to a container of a product having a constituent incompatible with said scented oils, said method comprising:
   (a) preparing an aqueous emulsion consisting essentially of:
      (1) from about 4% to about 70% of a polymer, said polymer being selected from a group consisting of water-emulsifiable polymers and water-soluble polymers,
      (2) from about 5% to about 80% of scented oils, and
      (3) from about 6% to about 80% of water;
   (b) drying said aqueous emulsion, whereby said scented oils are entrapped within a matrix of said polymer; and
   (c) including a coating of said polymer matrix on a surface of said container of said product, whereby said scented oils are protected by said polymer matrix from degradation by said constituent and diffuse from said polymer matrix over a period of time.

2. The method of claim 1 wherein said polymer is selected from the group consisting of vinyl polymers containing carbonyl or alcohol chemical groups, natural or synthetic rubbers, and mixtures thereof.

3. The method of claim 1 wherein said polymer is selected from the group consisting of polyvinyl acetate, polyacrylate, polymethacrylate, and mixtures thereof.

4. The method of claim 1 wherein said polymer is polyvinyl acetate.

5. The method of claim 1 wherein said incompatible constituent is an oxidative constituent.

6. The method of claim 3 wherein said incompatible constituent is an oxidative constituent.

7. The method of claim 5 wherein said oxidative constituent is a dry bleach.

8. The method of claim 6 wherein said oxidative constituent is a dry bleach.

9. The method of claim 7 wherein said dry bleach is an organic peroxygen bleach.

10. The method of claim 8 wherein said dry bleach is an organic peroxygen bleach.

11. The method of claim 7 wherein said aqueous emulsion comprises:
    (1) from about 4% to about 40% of said polymer;
    (2) from about 45% to about 80% of scented oils; and
    (3) from about 6% to about 45% of water.

12. The method of claim 10 wherein said aqueous emulsion comprises:
    (1) from about 10% to about 35% of said polymer;
    (2) from about 45% to about 65% of scented oils; and
    (3) from about 15% to about 40% of water.

13. A method for using scented oils to provide odor to a container of a product having a constituent incompatible with said scented oils, said method comprising:
    (a) preparing an adhesive aqueous emulsion consisting essentially of:
       (1) from about 4% to about 70% of a polymer, said polymer consisting of the group selected from water-emulsifiable polymers and water-soluble polymers,
       (2) from about 5% to about 80% of scented oils, and
       (3) from about 6% to about 80% of water;
    (b) spreading said aqueous emulsion on a surface to which said emulsion adheres;
    (c) drying said aqueous emulsion, whereby said scented oils are entrapped within a matrix of said polymer which is adhered to said surface; and
    (d) including said surface with said polymer matrix adhered thereto in said container with said product, whereby said scented oils are protected by said polymer matrix from degradation by said constituent and diffuse from said polymer matrix over a period of time.

14. The method of claim 13 wherein said polymer is selected from the group consisting of vinyl polymers containing carbonyl or alcohol chemical groups, natural or synthetic rubbers, and mixtures thereof.

15. The method of claim 13 wherein said polymer is selected from the group consisting of polyvinyl acetate, polyacrylate, polymethacrylate, and mixtures thereof.

16. The method of claim 13 wherein said polymer is polyvinyl acetate.

17. The method of claim 13 wherein said incompatible constituent is an oxidative constituent.

18. The method of claim 15 wherein said incompatible constituent is an oxidative constituent.

19. The method of claim 17 wherein said oxidative constituent is a dry bleach.

20. The method of claim 19 wherein said dry bleach is an organic peroxygen bleach.

21. The method of claim 18 wherein said oxidative constituent is an organic peroxygen bleach.

22. The method of claim 21 wherein said bleach is an aliphatic diperoxyacid having from about 6 to about 20 carbon atoms.

23. The method of claim 13 wherein said aqueous emulsion comprises:
    (1) from about 4% to about 40% of said polymer,
    (2) from about 45% to about 80% of scented oils, and
    (3) from about 6% to about 45% of water.

24. The method of claim 19 wherein said aqueous emulsion comprises:
    (1) from about 4% to about 40% of said polymer,
    (2) from about 45% to about 80% of scented oils, and
    (3) from about 6% to about 45% water.

25. The method of claim 18 wherein said aqueous emulsion comprises:
    (1) from about 4% to about 40% of said polymer,
    (2) from about 45% to about 80% of scented oils, and
    (3) from about 6% to about 45% of water.

26. The method of claim 21 wherein said aqueous emulsion comprises:

(1) from about 10% to about 35% of said polymer,
(2) from about 45% to about 65% of scented oils, and
(3) from about 15% to about 40% of water.

27. The method of claim 22 wherein said aqueous emulsion comprises:
(1) from about 10% to about 35% of said polymer,
(2) from about 45% to about 65% of scented oils, and
(3) from about 15% to about 40% of water.

28. The method of claim 17 wherein steps (a), (b) and (c) of said method are accomplished at temperatures below about 35° C.

29. The method of claim 26 wherein steps (a), (b) and (c) of said method are accomplished at temperatures below about 35° C.

30. The method of claim 17 wherein said surface is an inner surface of said container.

31. The method of claim 29 wherein said surface is an inner surface of said container.

32. The method of claim 30 wherein said container is a cardboard carton.

33. The method of claim 31 wherein said container is a cardboard carton.

34. An aqueous emulsion comprising:
(a) from about 4% to about 40% of a water-emulsifiable polymer;
(b) from about 45% to about 80% of scented oils; and
(c) from about 6% to about 45% of water.

35. The emulsion of claim 34 wherein said polymer is selected from the group consisting of vinyl polymers containing carbonyl or alcohol chemical groups, natural or synthetic rubbers, and mixtures thereof.

36. The emulsion of claim 34 wherein said polymer is selected from the group consisting of polyvinyl acetate, polyacrylate, polymethacrylate, and mixtures thereof.

37. The emulsion of claim 34 wherein said polymer is polyvinyl acetate.

38. The emulsion of claim 36 wherein said aqueous emulsion comprises:
(a) from about 10% to about 35% of said polymer;
(b) from about 45% to about 65% of scented oils; and
(c) from about 15% to about 40% of water.

39. The emulsion of claim 37 wherein said aqueous emulsion comprises:
(a) from about 10% to about 35% of said polymer;
(b) from about 45% to about 65% of scented oils; and
(c) from about 15% to about 40% of water.

40. The emulsion of claim 36 wherein said aqueous emulsion comprises:
(a) from about 20% to about 30% of said polymer;
(b) from about 45% to about 55% of scented oils; and
(c) from about 20% to about 30% of water.

* * * * *